United States Patent [19]

Johnson et al.

[11] Patent Number: 5,348,711
[45] Date of Patent: Sep. 20, 1994

[54] DENTAL HANDPIECE STERILIZER

[75] Inventors: Kenneth A. Johnson, Walworth; Steven W. White, Victor, both of N.Y.

[73] Assignee: MDT Corporation, Torrance, Calif.

[21] Appl. No.: 95,321

[22] Filed: Jul. 21, 1993

[51] Int. Cl.⁵ .............................. A61L 2/00; A61L 9/00
[52] U.S. Cl. ............................... 422/300; 134/166 R; 134/170; 422/292
[58] Field of Search .................... 422/28, 32-33, 422/292, 295, 301, 905, 300; 206/63.5, 368-370; 134/88-89, 170, 169 R, 92, 166 R; 433/114, 104, 132

[56] References Cited

U.S. PATENT DOCUMENTS

| 4,117,597 | 10/1978 | Trist et al. | 433/132 X |
| 4,544,355 | 10/1985 | Eibofner et al. | 433/104 |
| 4,752,444 | 6/1988 | Bowen et al. | 422/28 |
| 4,763,678 | 8/1988 | Oh | 134/171 |
| 4,923,522 | 5/1990 | Sowers | 134/22.1 |
| 4,990,087 | 2/1991 | DeRocchis et al. | 433/104 |
| 5,054,584 | 10/1991 | Hoffman | 184/55.1 |
| 5,057,283 | 10/1991 | Guggenheim et al. | 422/116 |
| 5,137,689 | 8/1992 | Cantrell | 422/28 |
| 5,165,503 | 11/1992 | Hoffman | 433/114 X |
| 5,225,160 | 7/1993 | Sanford et al. | 422/28 |

Primary Examiner—Robert J. Warden
Assistant Examiner—Krisanne M. Thornton
Attorney, Agent, or Firm—Trask, Britt & Rossa

[57] ABSTRACT

A dental handpiece sterilizer includes a sterilization chamber with an internal manifold system having outlet connectors into which dental handpieces can be plugged. A sterilant vapor introduced to the manifold flows through the dental handpieces coupled to the manifold and into the interior of the chamber so that it contacts the exterior surfaces of the handpieces before exiting the sterilant chamber.

11 Claims, 1 Drawing Sheet

DENTAL HANDPIECE STERILIZER

BACKGROUND OF THE INVENTION

1. Field The present invention relates to the sterilization of dental handpieces and particularly to sterilization apparatus that provides for the sterilization of both the inside and outside surfaces of dental handpieces.

2. State of the Art

The need to sterilize dental equipment, particularly dental handpieces, between uses has long been recognized. An urgency to provide more effective sterilization procedures has developed with the increasing awareness of the communicable disease hazards confronting dentists and their patients. These hazards include hepatitis, which is extremely difficult to treat, and AIDS, for which there is presently no effective cure. The AIDS epidemic has made dentists very aware that they, and their patients, may be exposed to the HIV virus through contact with blood and other body fluids.

One of the shortcomings of sterilization processes and apparatus conventionally used in the dental field is that the sterilant often fails to penetrate into the openings and passageways of dental handpieces. Dental handpieces may have a single internal passage or they may have a plurality of such passages. They are generally constructed to receive plug-in utility lines. These lines are coupled to the passages during use of a handpiece, and decoupled from the lines and the handpiece following use. When a handpiece is turned off, a slight vacuum is characteristically created at its tip. This suction tends to pull contaminant fluids, such as saliva and/or blood, into the internal passages of the handpiece. The separated handpiece is then subjected to a sterilization procedure, usually in a hermetically sealed chamber.

Chemical vapors are presently the sterilants of choice, because they provide a less corrosive environment than steam, but these vapors cannot effect adequate sterilization unless brought into intimate contact with the contaminating organisms under attack. Penetration is essential to achieve this contact, but no suitable system for providing such contact of chemical vapors to the internal surfaces of dental handpieces has been available.

U.S. Pat. No. 4,752,444 discloses a method for sterilizing a dental handpiece. According to that patent, a pneumatic pump is used to force a liquid sterilant through the interior of the handpiece. Next, a supply of water is pumped through the handpiece to flush away any sterilant residue. Then a supply of oil is passed through the handpiece to lubricate its mechanical components, suck as a turbine assembly or bearings. At the same time the liquid sterilant is passed through the dental handpiece, the exterior of the handpiece is soaked in a bath of sterilant.

U.S. Pat. No. 4,410,492, discloses a method which comprises the circulation of a sterilant gas through a contaminated medical device to sterilize exposed surfaces. The sterilant gas remains within the lumen of the device for an effective period of time, and thereafter is removed by purging with sterile air or other inert gas. The apparatus disclosed includes a chamber having an access door through which materials to be sterilized are introduced and removed, a pump, and control valves. In practicing the methods, a contaminated object, such as an endoscope, is placed in the chamber and is coupled to a discharge outlet. A pump is connected to the discharge outlet, outside the chamber. The chamber is sealed. Atmosphere is pumped from the chamber. The chamber is heated. A sterilant gas (ethylene oxide vapor) is circulated and recirculated, using the pump and valves, through and around the object for a time sufficient to effect sterilization. The sterilant is pulled through an opening at one end of the object, through the object and out an opening in an end of the object at the coupling to the chamber. The sterilant gas is removed, and sterile air or other gas is admitted, circulated around and through the object and out of the chamber through the pump and control valves.

U.S. Pat. No. 4,810,469 discloses a method for sterilizing an artificial organ with high pressure steam in an autoclave. Sterilized high pressure liquid, maintained at a temperature sufficient for sterilization, is passed through the artificial organ to raise its inner temperature to approximately a sterilization temperature. The organ is simultaneously heated externally to a sterilizing temperature, and is maintained at that temperature for the time required to sterilize the organ. A low temperature sterilant is then passed through and around the organ to cool it.

None of the sterilization systems currently available fill the need for apparatus that can be conveniently used in a dental office to sterilize equipment that is needed on a repeat basis throughout a working day. Particularly, there remains a need for a system that can quickly, easily and effectively sterilize the dental handpieces used by dentists with successive patients. Ideally, such a system should be suitable for the delivery of chemical vapor sterilant.

SUMMARY OF THE INVENTION

To accommodate the needs of dental operatories, there is provided an apparatus system that includes a sterilization chamber, a source of chemical vapor sterilant, and a source of purge fluid. The purge fluid of choice is currently filtered or sterilized air. A source of vacuum is used to help move the sterilant, and to remove air from the chamber, thereby effectively increasing the concentration of the sterilant. A manifold is connected to an inlet of the sterilization chamber through which the chemical vapor sterilant and purge fluid are directed. Socket couplings, spaced on the manifold, receive plugged-in dental handpieces such that chemical vapor sterilant and purge fluid entering the sterilization chamber are passed through the coupled handpieces to sterilize and cleanse the interior surfaces of such handpieces. The sterilant and purge fluid pass in turn through the inlet to the chamber, through the manifold and through coupled dental handpieces in the sterilization chamber.

Sterilant introduced to the inlet forces fluids from the internal passages of any handpieces connected to the manifold, and comes into direct contact with the interior surfaces of those passages. Upon exiting the handpieces, the sterilant is circulated around the handpieces to sterilize and cleanse their exterior surfaces.

A dental handpiece sterilizer of this invention will generally include a sealed sterilization chamber having an interior and an access door in sealable communication with the interior. An inlet fitting may extend through a wall of the chamber. Suitable coupler means may be positioned inside the sterilization chamber and connected to the inlet fitting. The coupler means will typically include at least one, usually a plurality of, outlet connectors. These connectors will ordinarily be structured and arranged for releasably coupling, as by plug-in connection, to a dental handpiece. The coupler means provides fluid pathways between the inlet and the connecters.

Sterilant supply means is constructed and arranged to introduce fluid sterilant to the inlet fitting. In this way, chemical sterilant introduced to the inlet fitting flows in turn through the coupler means, through each dental handpiece coupled to the coupler means and throughout the interior of the sterilization chamber, thereby to contact substantially the entire outer surface of each dental handpiece within the chamber.

A sterilizer outlet may be provided to control the rate of discharge of sterilant from the chamber. The impact on the pressure and phase relationships of the system, as predicted by the laws of thermodynamics, may be taken into consideration in conventional fashion. Control of the rates of introduction and discharge into and out of the system can be based upon sensor measurements of temperature and pressure levels in the chamber.

A pressure equalization conduit may interconnect the interior of the sterilant shot chamber and the interior of the sterilant supply reservoir, most desirably at the upper portions of each device.

The preferred sterilants are vaporized liquid chemical formulations. A typical means for supplying liquid chemical sterilant to the inlet fitting includes a liquid sterilant supply reservoir and a heated, temperature-controlled sterilant shot chamber in interruptable fluid flow communication with the reservoir. The shot chamber is operable to vaporize liquid sterilant. In a typical arrangement, first conduit means interconnects the reservoir and the shot chamber. This means, which may simply be a tube or hose, is in any event operable to convey liquid sterilant from the reservoir to the shot chamber. A first valve is connected in the system to control flow of liquid sterilant from the reservoir to the shot chamber through the first conduit. A second conduit is arranged to interconnect the shot chamber and the inlet fitting. A second valve is connected to control flow of vaporized sterilant from the sterilant shot chamber to the sterilization chamber through the second conduit. A third conduit may connect the interior of the sterilization chamber to a source of vacuum. In that event, a third valve may be connected to control flow through the third conduit. The third conduit may be associated with the primary sterilizer outlet or a secondary discharge outlet.

A manifold system may be included in the coupling means to distribute sterilant to one or more outlet connectors. The manifold will typically include a first primary fluid pathway. Structure associated with or integral with the manifold provides a second fluid pathway connecting the first fluid pathway to the inlet fitting inside the sterilization chamber. That structure is cooperatively adapted to the inlet fitting to facilitate their detachable coupling at the manifold. A plurality of connector lines, each having a proximal end, a distal end and an internal distribution channel, are also typical components of the manifold distribution system. The proximal end of each connector line may be connected to the manifold in fluid flow communication with the first fluid pathway. An outlet connector is carried by and connected in fluid flow communication with the distal end of each respective connector line. The outlet connectors couple, ideally in plug-in association, with dental handpieces.

An outlet connector is ordinarily provided with a plurality of delivery passages. The connector is usually structured to register selected of those delivery passages with corresponding internal passages of a dental handpiece. These internal passages are conventionally arranged in a prescribed pattern. The most common patterns accommodate either two or three passages. An adapter having a proximal end and a distal end may be used to adapt a connector having a greater number, e.g. three, of distribution passages to a dental instrument having a smaller number of internal passages. The proximal end of the adapter is interfaced with the outlet connector, while the distal end is structurally interfaced with a the dental handpiece. The adapter itself is structured and arranged to block fluid flow through the delivery passage(s) which is (are) not in registration with an internal passage of the handpiece. It is within contemplation to similarly adapt from a smaller number of distribution passages up to a larger number of internal handpiece passages.

DESCRIPTION OF THE ILLUSTRATED EMBODIMENT

Figure 1:
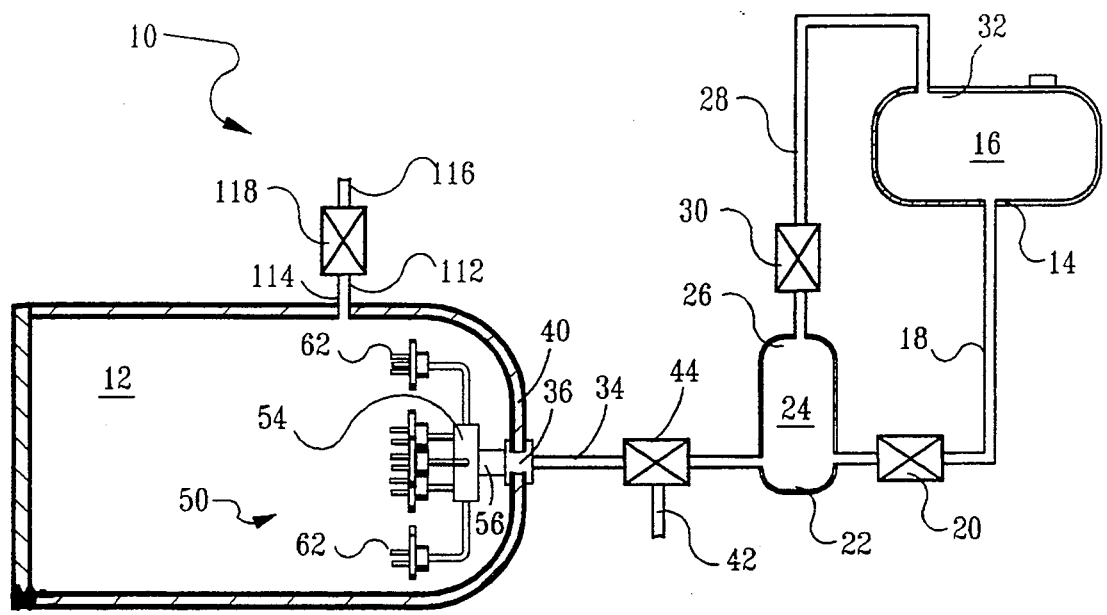
FIG. 1 is a schematic representation of the dental handpiece sterilization system of the invention.

A dental handpiece sterilization system 10 of the invention includes a sterilization chamber, shown generally at 12. A bottom 14 of a sterilant supply reservoir 16 is connected by a conduit 18, through a first valve 20, to the bottom 22 of a heated sterilant shot chamber 24. A top 26 of the shot chamber 24 is connected by a conduit 28 through a pressure equalization valve 30 to a top 32 of the sterilant supply reservoir 16. A conduit 34 connects the bottom of the shot chamber 24 with an inlet fitting 36 that extends through a rear wall 40 of the sterilization chamber 12.

A conduit 42 connects a control valve 44 in the line 34 with a source of purge fluid (not shown). The purge fluid may be filtered air, sterilized air or other gas. It may be either separately provided or taken from any source of such purge fluid available in the dental operatory. In typical practice, filtered air is relied upon to purge any residual chemical vapors remaining following the sterilization phase.

A manifold 50 includes a central T-fitting 54 having a central projection 56. The central projection 56 forms a plug connector adapted to the inlet fitting 36, inside the sterilization chamber 12. A plurality of connector lines 58, here shown as six, five being visible, each have a first end 60 connected into the main line 52. Each line 58 has a connector 62 on a second end 64. Four of the lines 58 include a lateral extension 66 which assures adequate spacing of the connectors 62.

Figure 2:
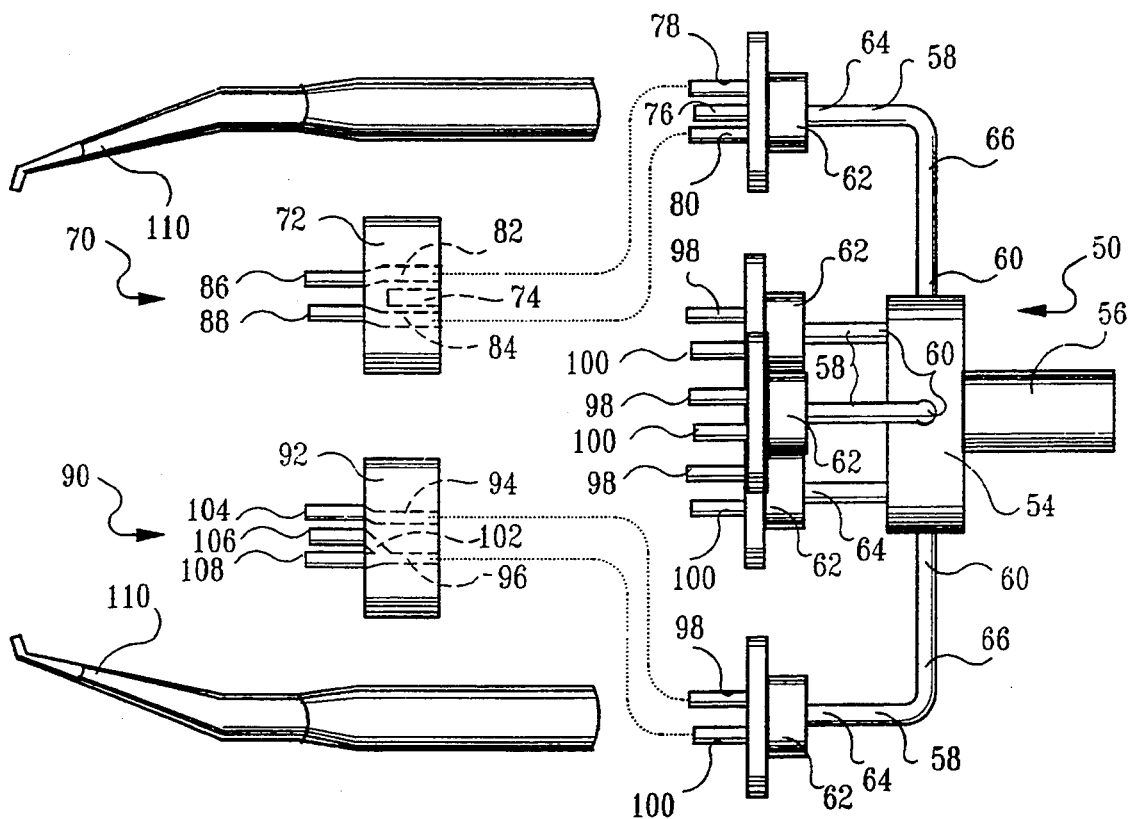
FIG. 2 is an enlarged, exploded side elevation view of dental handpieces in association with components of the system of this invention.

The connectors 62 may provide for either two- or three-hole communication as required to accommodate different handpiece designs. One or more of the connectors 62 may be dedicated for use with two-hole communication. Likewise, one or more of the connectors 62 may be dedicated for use with three-hole communication. Alternatively, the connectors may all be three-hole connectors and adapters may be used to plug one hole and to connect the others to the common two-hole handpieces. Such an adapter is shown at 70, in FIG. 2.

Adapter 70 has a block housing 72 with a blind bore 74 in one end to fit over the line 76 of the three-hole connector 62 that is to be blocked off by the adapter. The other two lines 78 and 80 of the connector 62 extend into bores 82 and 84, respectively, through the housing. The bores 82 and 84 extend through the housing 72 to short conduits 86 and 88 that are adapted to fit into the inlets of common two-hole handpieces.

Another adapter 90 has a block housing 92 with two bores 94 and 96 arranged to receive the two conduits 98 and 100 from a two-hole connector. A third bore 102 extends through the block housing 92 so that the bores 94, 96, and 102, respectively, terminate in short conduits 104, 106, and 108 that are adapted to fit into the inlets of the common three-hole handpieces.

Whether two-hole or three-hole handpieces, the handpieces, which are shown at 110 removed from the connectors 62, are coupled to the connectors 62 for sterilization purposes. Handpieces 110 may be coupled to connectors 62 before the manifold 50 is placed in the sterilization chamber 12 and central projection 56 is plugged into inlet fitting 36. Alternatively, the manifold 50 may be placed in the sterilization chamber 12, with the central projection plugged into the inlet 36 before handpieces 110 are coupled to connectors 62. It will be apparent that the manifold 50 may also be permanently connected to the inlet fitting 36.

A vacuum conduit 112 has one end 114 connected into the sterilization chamber 12 and an opposite end 116 connected to a source of vacuum (not shown). A valve 118 is provided in the conduit 112. The source of vacuum may be the house vacuum source common in virtually all dental operatories.

In operation, the valve 118 is opened to create a vacuum, typically between about 1 to about 5 psia, in the chamber 12. Liquid chemical sterilant is placed in the sterilant supply reservoir 16. Under control of the valve 20, the liquid sterilant is allowed to flow from the reservoir 16, by gravity, into the heated, temperature-controlled sterilant shot chamber 24. The sterilant is heated in chamber 24 to produce a heated sterilant mixture in a vapor phase, at a pressure above atmospheric. Vaporized sterilant from the chamber 24 flows through conduit 34, under control of valve 44, and through the inlet fitting 36. The sterilant then flows through the central projection 56, into the main line 52 of the manifold 50, through the connector lines 58, connectors 62, adapters 70 and/or 90, if used, and through handpieces 110 coupled to the connectors 62. The vaporized sterilant flows from the shot chamber 24 because of the increased pressure developed in the shot chamber during heating and vaporization of the sterilant and the reduced pressure created in the sterilization chamber 12 upon opening of the valve 118.

After passing through the manifold 50 and any handpieces 110 coupled to connectors 62, the vaporized sterilant fills the sterilization chamber 12 and is allowed to remain in contact for a prescribed period of time with the exterior surfaces of the coupled handpieces before flowing out of the sterilization chamber through line 112.

After the handpieces 110 have been sterilized inside and out by exposure to the vaporized sterilant for a required time period, valve 44 is operated to cut off flow from the shot chamber 24 to the sterilization chamber 12. Thereafter, valve 44 is operated to connect the purge fluid conduit 42 to the inlet fitting 36 and the manifold 50. The purge fluid (typically air) flows through the manifold and the handpieces 110 coupled to connectors 62, into the sterilization chamber 12, through and around the handpieces 110 and out the conduit 112. A replaceable filter (not shown) may be positioned in the conduit 94 during the purge phase.

The present invention provides sterilization apparatus particularly suited for the easy, thorough sterilization of dental handpieces. The apparatus of the invention is adaptable for use with other dental operatory equipment, can be made to be compact, and will accommodate simultaneous inside and exterior sterilization of a number of dental handpieces.

While a preferred embodiment of the invention has been herein described, variations are contemplated within the scope of the appended claims, which themselves recite those features regarded as important to the invention.

What is claimed is:

1. A dental handpiece sterilizer comprising:
   a sealed sterilization chamber having an interior and an access door in sealable communication with said interior;
   an inlet fitting extending through a wall of said sterilization chamber; and
   coupler means fixed inside said sterilization chamber and connected to said inlet fitting, said coupler means including a rigid outlet connector, said outlet connector being structured and arranged for releasably coupling to a plurality of dental handpieces, said coupler means further including fluid pathways between said inlet fitting and said connecter and through said connector to the interior of each connected dental handpiece; sterilant supply means constructed and arranged to introduce vaporized sterilant to said inlet fitting; whereby sterilant introduced to said inlet fitting flows through said coupler means, through each dental handpiece coupled to said coupler means and throughout said interior of said sealed sterilization chamber, thereby to contact substantially the entire outer surface of each dental handpiece within said sterilization chamber;
   and valve controlled vacuum means opening into said chamber.

2. A dental handpiece sterilizer according to claim 1, wherein said means for supplying sterilant to said inlet fitting comprises:
   a liquid sterilant supply reservoir;
   a heated, temperature-controlled sterilant shot chamber in interruptable fluid flow communication with said reservoir, said shot chamber being operable to vaporize liquid sterilant;
   first conduit means interconnecting said reservoir and said shot chamber, operable to convey liquid sterilant from said reservoir to said shot chamber;
   first valve means operable to control flow of liquid sterilant from said reservoir to said shot chamber through said first conduit means;
   second conduit means interconnecting said shot chamber and said inlet fitting; and
   second valve means operable to control flow of vaporized sterilant from said sterilant shot chamber to said sealed sterilization chamber through said second conduit means.

3. A dental handpiece sterilizer according to claim 2, further comprising:

third conduit means opening into said sealed sterilization chamber for connection to a source of vacuum; and third valve means controlling flow through said third conduit means.

4. A dental handpiece sterilizer according to claim 3, wherein said coupler means includes:

a manifold having a first fluid pathway, connector means including a second fluid pathway connecting said first fluid pathway to said inlet fitting inside said sterilization chamber, and a plurality of connector lines, each having a proximal end, a distal end and an internal distribution channel, the proximal end of each said connector line being connected to said manifold in fluid flow communication with said first fluid pathway; and said outlet connector being connected in fluid flow communication with said distal end of each respective said connector line.

5. A dental handpiece sterilizer according to claim 4, wherein:

said connector means is operatively adapted to said inlet fitting to facilitate their detachable coupling.

6. A dental handpiece sterilizer according to claim 5, further including:

a pressure equalization conduit interconnecting an inside top of said sterilant shot chamber and an inside top of said sterilant supply reservoir; and a pressure equalization valve in said pressure equalization conduit.

7. A dental handpiece sterilizer according to claim 4, wherein:

said outlet connector has a plurality of delivery passages structured to register selected said delivery passages with corresponding internal passages of a dental handpiece; and an adapter, having a proximal end and a distal end, said proximal end being structurally interfaced with said outlet connector, said distal end being structurally interfaced with a said dental handpiece, and said adapter being structured and arranged to block fluid flow through one of said delivery passages which is not currently in registration with a said internal passage.

8. A dental handpiece sterilizer according to claim 1, wherein said coupler means includes:

a manifold having a first fluid pathway, connector means including a second fluid pathway connecting said first fluid pathway to said inlet fitting inside said sterilization chamber, and a plurality of connector lines, each having a proximal end, a distal end and an internal distribution channel, the proximal end of each said connector line being connected to said manifold in fluid flow communication with said first fluid pathway; and said outlet connector being connected in fluid flow communication with said distal end of each respective said connector line.

9. A dental handpiece sterilizer according to claim 8, including:

said outlet connector has a plurality of delivery passages structured to register selected said delivery passages with corresponding internal passages of a dental handpiece; and an adapter, having a proximal end and a distal end, said proximal end being structurally interfaced with said outlet connector, said distal end being structurally interfaced with a said dental handpiece, and said adapter being structured and arranged to block fluid flow through one of said delivery passages which is not in registration with a said internal passage.

10. A dental handpiece sterilizer according to claim 9, further including:

sterilant supply means constructed and arranged to introduce chemical sterilant to said inlet fitting; whereby chemical sterilant introduced to said inlet fitting flows through said coupler means, through each of at least one dental handpiece coupled to said coupler means and throughout said interior of said sterilization chamber, thereby to contact substantially the entire outer surface of each dental handpiece within said sterilization chamber.

11. A dental handpiece sterilizer according to claim 10, including a sterilizer outlet operable to discharge sterilant from said interior at a selected rate.

* * * * *